US00PP22028P2

(12) United States Plant Patent
Kanaya

(10) Patent No.: US PP22,028 P2
(45) Date of Patent: Jul. 12, 2011

(54) ***CALIBRACHOA* PLANT NAMED 'SUNCALKULEMO'**

(50) Latin Name: ***Calibrachoa* sp.**
Varietal Denomination: Suncalkulemo

(75) Inventor: Takeshi Kanaya, Shiga (JP)

(73) Assignee: Suntory Flowers, Ltd., Tokyo (JP)

( * ) Notice: Subject to any disclaimer, the term of this patent is extended or adjusted under 35 U.S.C. 154(b) by 0 days.

(21) Appl. No.: 12/658,732

(22) Filed: Feb. 12, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Kent L Bell
(74) *Attorney, Agent, or Firm* — C. A. Whealy

(57) ABSTRACT

A new and distinct cultivar of *Calibrachoa* plant named 'Suncalkulemo', characterized by its outwardly spreading to trailing plant habit; vigorous growth habit; freely branching and flowering plant habit; early and long flowering period; yellow-colored flowers; and good garden performance.

1 Drawing Sheet

Botanical designation: *Calibrachoa* sp.
Cultivar denomination: 'SUNCALKULEMO'.

BACKGROUND OF THE INVENTION

The present invention relates to a new and distinct cultivar of *Calibrachoa* plant, botanically known as *Calibrachoa* sp. and hereinafter referred to by the name 'Suncalkulemo'.

The new *Calibrachoa* plant is a product of a planned breeding program conducted by the Inventor in Higashiomi, Shiga, Japan. The objective of the breeding program is to develop new trailing and freely-branching *Calibrachoa* plants with attractive and unique flower coloration.

The new *Calibrachoa* plant originated from a cross-pollination conducted by the Inventor in Higashiomi, Shiga, Japan in April, 2005 of a proprietary selection of *Calibrachoa* sp. identified as code number CR1, not patented, as the female, or seed, parent with a proprietary selection of *Calibrachoa* sp. identified as code number CS1, not patented, as the male, or pollen, parent. The new *Calibrachoa* plant was discovered and selected by the Inventor as a single flowering plant from within the progeny of the stated cross-pollination in a controlled greenhouse environment in Higashiomi, Shiga, Japan in September, 2006.

Asexual reproduction of the new *Calibrachoa* plant by vegetative cuttings in a controlled greenhouse environment in Higashiomi, Shiga, Japan since October, 2006, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Suncalkulemo'. These characteristics in combination distinguish 'Suncalkulemo' as a new and distinct cultivar of *Calibrachoa:*

1. Outwardly spreading to trailing plant habit.
2. Vigorous growth habit.
3. Freely branching and flowering plant habit.
4. Early and long flowering period.
5. Yellow-colored flowers.
6. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are more trailing than plants of the female parent selection.
2. Plants of the new *Calibrachoa* and the female parent selection differ in flower color as plants of the female parent selection have red-colored flowers.

Plants of the new *Calibrachoa* can be compared to plants of the male parent selection. Plants of the new *Calibrachoa* differ primarily from plants of the male parent selection in growth habit as plants of the new *Calibrachoa* are more trailing than plants of the male parent selection.

Plants of the new *Calibrachoa* can also be compared to plants of 'Sunbelki', disclosed in U.S. Plant Pat. No. 11,558. In side-by-side comparisons conducted in Higashiomi, Shiga, Japan, plants of the new *Calibrachoa* and 'Sunbelki' differed primarily in the following characteristics:

1. Plants of the new *Calibrachoa* were more trailing than and not as upright as plants of 'Sunbelki'.
2. Plants of the new *Calibrachoa* were shorter than plants of 'Sunbelki'.
3. Plants of the new *Calibrachoa* were more freely branching than plants of 'Sunbelki'.
4. Leaves of plants of the new *Calibrachoa* were narrower than leaves of plants of 'Sunbelki'.
5. Flower corollas of plants of the new *Calibrachoa* did not have conspicuous venation whereas flower corollas of plants of 'Sunbelki' had conspicuous venation.

BRIEF DESCRIPTION OF THE PHOTOGRAPHS

The accompanying colored photographs illustrate the overall appearance of the new *Calibrachoa* plant, showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Suncalkulemo' grown in a container.

The photograph at the bottom of the sheet is a close-up view of typical leaves and flowers of 'Suncalkulemo'.

DETAILED BOTANICAL DESCRIPTION

The aforementioned photographs and following observations, measurements and values describe plants grown in 15-cm containers in Higashiomi, Shiga, Japan, under commercial practice during the early summer in an outdoor nursery. During the production of the plants, day temperatures averaged 23° C. and night temperatures averaged 13° C. Plants had been growing for four and five months when the description and photographs, respectively, were taken. In the following description, color references are made to The Royal Horticultural Society Colour Chart, 2001 Edition, except where general terms of ordinary dictionary significance are used.

Botanical classification: *Calibrachoa* sp. 'Suncalkulemo'.

Parentage:

*Female, or seed, parent.*—Proprietary selection of *Calibrachoa* sp. identified as code number CR1, not patented.

*Male, or pollen, parent.*—Proprietary selection of *Calibrachoa* sp. identified as code number CS1, not patented.

Propagation:

*Type.*—By vegetative cuttings.

*Time to initiate roots.*—About one week at 15° C. to 20° C.

*Time to produce a rooted young plant.*—About three weeks at 15° C. to 20° C.

*Root description.*—Fibrous; white in color.

*Rooting habit.*—Freely branching.

Plant description:

*Plant and growth habit.*—Outwardly spreading to trailing and mounding plant habit; freely branching habit with numerous lateral branches developing per plant; pinching enhances lateral branch development; vigorous growth habit.

*Plant height.*—About 12 cm.

*Plant diameter.*—About 39.5 cm.

Lateral branch description:

*Length.*—About 17 cm.

*Diameter.*—About 1.4 mm.

*Internode length.*—About 1.4 cm.

*Strength.*—Strong.

*Aspect.*—Decumbent.

*Texture.*—Pubescent.

*Color.*—Close to 145A.

Foliage description:

*Arrangement.*—Alternate, simple.

*Length.*—About 3 cm.

*Width.*—About 1.1 cm.

*Shape.*—Elliptic.

*Apex.*—Broadly acute.

*Base.*—Obtuse to cuneate.

*Margin.*—Entire.

*Texture, upper and lower surfaces.*—Pubescent.

*Venation pattern.*—Pinnate; reticulate.

*Color.*—Developing and fully expanded leaves, upper surface: Close to 138A; venation, close to 145A. Developing and fully expanded leaves, lower surface: Close to 138B; venation, close to 145A.

*Petiole.*—Length: About 2.4 mm. Diameter: About 1.6 mm. Texture, upper and lower surfaces: Pubescent. Color, upper and lower surfaces: Close to 145A.

Flower description:

*Flower arrangement and habit.*—Single salverform flowers arising from upper leaf axils; freely flowering habit with usually about 60 flowers per plant; flowers face upright or outwardly.

*Fragrance.*—None detected.

*Natural flowering season.*—Early flowering habit, plants of the new *Calibrachoa* initiate and develop flowers about three to four weeks after planting; long flowering period, flowering commences naturally during the spring and plants flower continuously throughout the summer until late autumn in Japan.

*Flower longevity.*—Individual flowers last about seven to ten days on the plant; flowers not persistent.

*Flower diameter.*—About 2.8 cm.

*Flower length (depth).*—About 2.4 cm.

*Throat diameter.*—About 7.8 mm.

*Tube length.*—About 1.6 cm.

*Tube diameter, base.*—About 1.9 mm.

*Flower bud.*—Shape: Cylindrical. Length: About 1.7 cm. Diameter: About 4.7 mm. Color: Close to 150D.

*Corolla.*—Arrangement: Five petals fused at the base and opening into a flared trumpet. Petal length from throat: About 1 cm. Petal width: About 1 cm. Petal shape: Spatulate. Petal apex: Rounded. Petal margin: Entire. Petal texture, upper and lower surfaces: Smooth, glabrous. Throat texture: Smooth, glabrous. Tube texture: Pubescent. Color: Petal, when opening and fully opened, upper surface: Close to 7A. Petal, when opening and fully opened, lower surface: Close to 9D. Throat: Close to 12B. Tube: Close to 1B.

*Calyx.*—Arrangement: One star-shaped calyx tube with five sepals fused at the base. Sepal length: About 7.3 mm. Sepal width: About 2.6 mm. Sepal shape: Lanceolate. Sepal apex: Acute. Sepal margin: Entire. Sepal texture, upper and lower surfaces: Pubescent. Sepal color: Immature and mature, upper surface: Close to 143A. Immature and mature, lower surface: Close to 143A.

*Peduncles.*—Length: About 1.9 cm. Diameter: About 0.7 mm. Angle: Upright to outwardly. Strength: Strong. Texture: Pubescent. Color: Close to 144B.

*Reproductive organs.*—Stamens: Quantity/arrangement: Five per flower. Stamen length: About 8.5 mm. Anther shape: Ellipsoidal. Anther length: About 1.5 mm. Anther diameter: About 1 mm. Anther color: Close to 10C. Pollen amount: Moderate. Pollen color: Close to 10C. Pistils: Quantity: One per flower. Pistil length: About 9.5 mm. Style color: Close to 144D. Stigma shape: Transversely ellipsoidal. Stigma color: Close to 144C. Ovary color: Close to 144C.

*Seed/fruit.*—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen/pest resistance: Plants of the new *Calibrachoa* have not been observed to be resistant to pests and pathogens common to *Calibrachoa* plants.

It is claimed:

1. A new and distinct *Calibrachoa* plant named 'Suncalkulemo' as illustrated and described.

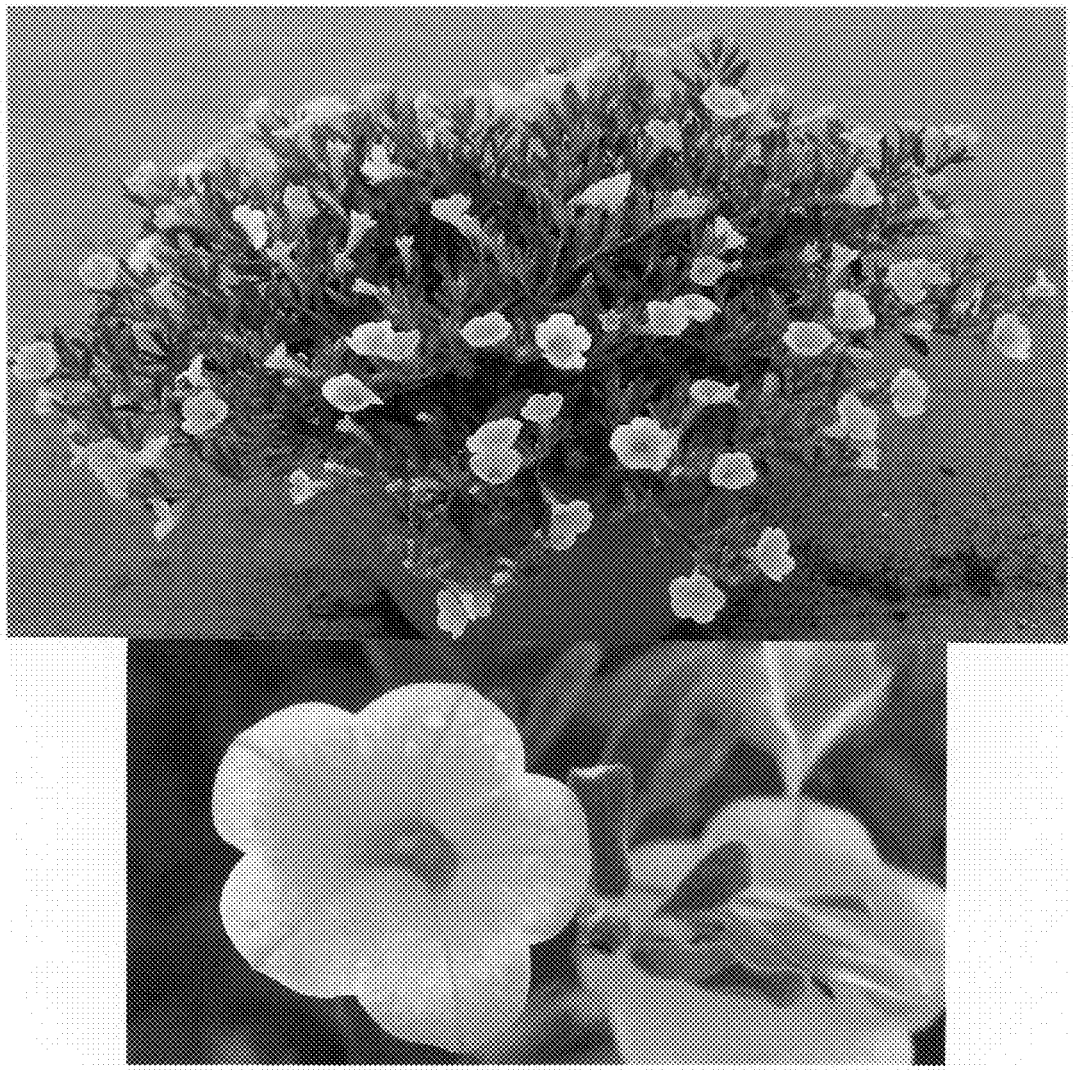

* * * * *